United States Patent
Saxena et al.

(10) Patent No.: US 7,741,108 B2
(45) Date of Patent: Jun. 22, 2010

(54) BACTERIA SENSOR AND METHOD

(75) Inventors: Indu Saxena, Torrance, CA (US); Herbert Shapiro, Laguna Miguel, CA (US)

(73) Assignee: Optech Ventures, LLC, Torrance, CA (US)

( * ) Notice: Subject to any disclaimer, the term of this patent is extended or adjusted under 35 U.S.C. 154(b) by 1112 days.

(21) Appl. No.: 11/395,849

(22) Filed: Mar. 31, 2006

(65) Prior Publication Data

US 2006/0254343 A1 Nov. 16, 2006

Related U.S. Application Data

(63) Continuation-in-part of application No. 11/035,501, filed on Jan. 14, 2005, now abandoned.

(51) Int. Cl.
C12M 1/34 (2006.01)
C12M 3/00 (2006.01)
(52) U.S. Cl. .................................. 435/288.7
(58) Field of Classification Search ................ 73/53.01; 422/82.08; 435/288.7
See application file for complete search history.

(56) References Cited

U.S. PATENT DOCUMENTS

| | | | | |
|---|---|---|---|---|
| 5,049,492 | A * | 9/1991 | Sauer et al. | 435/30 |
| 5,470,949 | A * | 11/1995 | Polt | 530/322 |
| 5,947,959 | A | 9/1999 | Sinofsky | |
| 6,044,981 | A | 4/2000 | Chu et al. | |
| 6,197,575 | B1 * | 3/2001 | Griffith et al. | 435/288.4 |
| 6,426,505 | B1 | 7/2002 | Rao et al. | |
| 6,800,478 | B2 | 10/2004 | Castellini | |

(Continued)

OTHER PUBLICATIONS

T.F. Cooney et al., Comparative Study of Some Fiber-Optic Remote Raman Probe Designs. Part I and II, Applied Spectroscopy, 1996, p. 836-860, vol. 50(7).

(Continued)

*Primary Examiner*—Walter D Griffin
*Assistant Examiner*—Shanta G Doe
(74) *Attorney, Agent, or Firm*—Lawrence S. Cohen

(57) ABSTRACT

Bacteria accumulations on the interior walls of a fluid conduit are detected by placing a bacterial target substrate in the conduit. The substrate is structured to allow bacteria to colonize it at at least the rate of accumulation expected on the conduit walls or at an accelerated rate in order to preempt normal bacteria accumulation on the walls. A bacteria getter may be used to accelerate bacterial colonization of the substrate. An excitation signal interrogating the substrate causes autofluorescence in the presence of bacteria, specifically from NADH and/or NADPH present. The autofluorescent emission is transmitted to a detector and processor. In one system when the presence of bacteria at a preset level is detected there is initiated a diversion of the fluid into an auxiliary subsystem during which the primary subsystem is remediated. In one configuration, a wall portion is transparent and the biofilm target substrate is integral with the transparent wall portion and the sensor head is attached to the outside of the transparent wall portion. It can be made as a removable and/or disposable cell in which the transparent wall portion is a glass plug that fits into a hole in the conduit. The biofilm target substrate can be a getter affinity surface formed on the inside surface of the glass plug. Various means are used for obtaining accelerated biofilm growth.

8 Claims, 11 Drawing Sheets

U.S. PATENT DOCUMENTS

| | | |
|---|---|---|
| 7,190,457 B2 | 3/2007 | Tobacco et al. |
| 2005/0151971 A1* | 7/2005 | Tabacco et al. ............ 356/417 |
| 2008/0058908 A1 | 3/2008 | Bornstein |

OTHER PUBLICATIONS

L. Jacobs et al., Spectrophotometric monitoring of biofouling, Wat. Sci. Tech., 1996, p. 533-540, vol. 34, Elsevier Science Ltd, Great Britain.

J. Kelstrup et al., Microbial aggregate contamination of water lines . . . and its control, Acta Pathol. Microbiol. Scand. Sect. B Microbil., 1977, p. 177-183, vol. 85.

M.V. Martin, The significance of the bacterial contamination . . . water systems, British Dental Journal, 1987, p. 152-154, vol. 163.

J.A. Mayo et al., Bacterial Biofilm: A Source of Contamination in Dental Air-Water Syringes, Clinical Preventive Dentistry, 1990, p. 13-20, vol. 12.

G.A. McFeters et al., Rapid direct methods for enumeration of specific . . . water and biofilms, Journal of Applied Microbiology, 1999, p. 193-200, vol. 85 (supplement).

K. Pedersen, Method for studying microbial biofilms in flowing-water systems, Applied and Environmental Microbiology, 1982, p. 6-13, vol. 43.

D.L. Pierson, Automated Use of DNA Probes for Rapid Detection of Bacteria in Water, http://peer1.idi.usra.edu/peer_review/taskbook/life_science/ls00/ltb_proj_list.cfm, Jun. 1, 2001.

B.D. Tall et al., Bacterial succession within a biofilm in water supply lines of dental air-water syringes, Canadian J. of Microbiology, 1995, p. 647-654, vol. 41, Canada.

U. Utzinger et al., Fiber optic probes for biomedical optical spectroscopy, Journal of Biomedical Optics, 2003, p. 121-147, vol. 8(1).

J.F. Williams et al., Microbial contamination of dental unit water lines: prevelance, intensity and microbiological characteristics, J. Am. Dent. Assoc.,1993, p. 59-65, vol. 124.

Bass, Michael, Handbook of Optics, vol. II, Second Edition, McGraw-Hill, Inc. New York.

* cited by examiner

BACTERIA SENSOR AND METHOD

RELATED APPLICATIONS

This application is continuation-in-part of application Ser. No. 11/035,501 filed on Jan. 14, 2005 now abandoned the entire content of which is incorporated herein by reference.

FIELD OF THE INVENTION

This invention relates to the detection of bacteria accumulations (referred to herein as biofilm) on the interior walls of tubes or conduits carrying fluids in which bacteria are entrained.

BACKGROUND OF THE INVENTION

There is a wide range of situations where biofilm growth is a problem. A biofilm detection instrument will have numerous applications. Conventional procedures, where samples must be taken from a possibly colonized area and analyzed by trained personnel are slow and expensive.

Water lines frequently accumulate bacteria on the interior walls of the line. When used in medical and/or dental or other hygienic related application the accumulation of bacteria on surfaces often leads to user infections and, for remediation, equipment down time.

The problem is particularly noticeable, for example, in dental offices where water lines are used in oral irrigation systems. Bacteria freely moving in the water can be removed by filters and cause no problem. But, the problem arises when some of the bacteria starts to accumulate as biofilm at some point along the interior wall of the line.

Typically bacterial accumulation tends to occur first at an obstruction such as a bend or discontinuity in the line or a change in the geometry of the line as might be introduced by a clamp, joint or some connection to the line.

Also fluid line used in hemodialysis, similar serious problems exist.

Also, the presence of bacteria in food processing equipment also causes biofilm deposits at critical points such as pumps, valves, bends, and heat exchangers.

There are numerous other cases where bacteria in fluid lines creates risk of passing bacteria downstream to end users caused by biofilm.

There is a need for technology to avoid the growth of excessive biofilm and to remediate it in fluid systems. A real time, on-line system and d method has not been available.

The present invention in one aspect provides an apparatus and method for detecting the growth and presence of biofilm and for on-line remediation.

Previous methods of biofilm detection have required physical access to the interior of subject conduits in order to detect, analyze and measure biofilm in conduits. Such methods are inconvenient at best and often require that the system be shut down. Further since the level of biofilm on system conduits that is regarded as intolerable cannot be determined with accuracy, remediation is often scheduled sufficiently in advance as to ensure that the intolerable level has not been reached. This of course means that the cycle of remediation must take place well before it may actually be necessary, or worse that it may be put off beyond the tolerable level of biofilm growth.

Consequently systems and methods are desirable that can remotely and continuously detect, monitor and evaluate the level and the rate of biofilm growth in conduits. Further in such systems it is desirable to be able to anticipate the time that remediation is required by detecting an accelerated growth of biofilm at a monitoring location.

BRIEF DESCRIPTION OF THE INVENTION

The invention is an apparatus and method for fiber optic biological detection of biofilm bacterial contamination of fluid carrying lines, in particular water lines. In one aspect the invention comprehends a low cost easy to use fiber optic based system, which can monitor biofouling of water lines or other fluid carrying lines at one or more points simultaneously.

In accordance with one aspect of the invention light beam of selected wavelength is directed at a selected site at which the presence of biofilm is to be detected, the light being of a nature to cause autofluorescence of bacteria at the site (excitation light). The autofluorescence is detected indicating the presence of live bacteria. The autofluorescence is referred to as emission light. In a further aspect, a substrate is placed in a selected location in a fluid line in which the presence of bacterial biofilm accumulation is desired to be detected. The substrate acts as a colonization site for bacteria. A fiber optic cable is placed a working distance from the substrate. One or more optical fibers in the cable carry excitation light directed onto the substrate. The excitation light is of a selected wavelength to cause autofluorescence of bacteria. In the presence of bacteria, the autofluorescence will occur and the consequent excitation light or signal is detected by other optical fibers, preferably in the same cable and transmitted to a detection unit.

The substrate should be of a material that will not itself autofluorescence in the presence of the excitation light directed at the substrate. It should also be of a material that will allow colonization of bacteria at a rate at least as fast as, and preferably faster than, the accumulation of bacteria on the fluid line. In this way remediation can be planned in advance of serious excess biofilm presence in the fluid line.

The amount of biofilm accumulation on the substrate can be measured by the relative intensity of the emission signal.

In accordance with one aspect of this invention, the substrate comprises a bacteria getter configured to attract bacteria at a rate that is relatively fast compared to the rate at which line obstructions or geometric changes attract bacteria. A bacteria getter refers to special structure that will capture, attract or otherwise cause the accumulation of bacteria other than by the normal colonization of a surface. For example a fine mesh through which bacteria cannot pass would be regarded as a bacteria getter. Also a substrate treated with a bacteria attracting chemistry such as agar would be similarly regarded as a bacteria getter. It is noted that in some applications the introduction of an extraneous chemistry would not be acceptable.

The accumulation of bacteria on the substrate results in autofluorescence at a frequency different from the frequency of light directed at the substrate. Light is directed at the substrate to sample for bacteria accumulation. A detector operatively coupled to the substrate responds to the light at the autofluorescence frequency to provide a signal indicative of the presence of bacteria.

However, the excitation light does create an undesirable noise level in the returning emission light and therefor a filter in employed to remove the returning excitation light.

In one aspect, the emission signal provided by the detector is operative to activate a mechanism for diverting fluid flow into a second fluid line and for introducing a bactericidal agent into the first fluid line. Alternatively, an infrared energy delivery system can be used to heat the substrate at a temperature and for a time to destroy the bacteria.

Further aspects of the invention involve use of a transparent wall portion exposed to the fluid in the fluid system. The sensor head is installed on the outside surface of the wall portion and the biofilm target substrate is integral with the inside surface of the transparent wall. Consequently the excitation signal and the returning emission signal pass only through the transparent wall, and not through and portion of the fluid. In one configuration a transparent conduit portion is installed in the fluid system. In another configuration a sensing cell has a transparent wall portion shaped to fit in an aperture made in a fluid carrying conduit. On the outside surface a receptacle is mounted for receiving the optical fiber sensing head. On the inside surface the biofilm target substrate is integral with the transparent wall.

The biofilm target substrate may be rendered a getter affinity surface in order to promote accelerated biofilm growth by either physical configurations such as cavities or chemistry such as by sticky glycosides.

DETAILED DESCRIPTION

Attached to the application of which this is a continuation-in-part is a document entitled FINAL REPORT, the entire content of which is incorporated by reference into this description.

Bacteria are one of nature's most abundant and viable life forms. Sessile forms of bacteria form biofilms on surfaces and can nurture additional pathogens. These biofilms can cause major health problems when infesting man-made medical delivery systems that should ideally, be sterile. Further, the infestation of bacteria on fluid lines of many types of systems is undesirable. At least, in many systems, it is desirable to be able to monitor the accumulation of bacteria on the conduit surfaces and to remediate the collection of bacteria in the conduit. Therefore the on-line in-situ detection of biofilm accumulation and measurement of the degree of biofilm accumulation is useful. For example systems such as water delivered by dental equipment, and in hemodialysis facilities should be monitored for bacteria accumulation and when appropriate remediated.

The invention as described herein is an apparatus and method for on-line, in-situ detection of bacteria accumulation on a substrate placed in the fluid line by means of a bacterial target such as a bacteria collecting substrate and an excitation light that is delivered by one or more optical fibers that will cause autofluorescence of the bacteria and an optical fiber receiver that will receive the autofluorescence emission signal. The excitation optical fiber carrying the excitation signal and the receiving optical fiber carrying the emission signal extend from a source and a receiver/processor respectively. The source provides a light of appropriate frequency to cause the autofluorescent response from the bacteria (it is again noted that the autofluorescence is from NADH and/or NADPH present with the bacteria). The receiver/processor receives the emission signal and may be equipped to monitor and record signals over time when the system is configured for automatic operation; and may also be equipped to measure different intensity of the emission signal and compare it to a reference signal and to signals earlier in time to enable tracking or to a signal level set as an alarm level.

Figure 1:
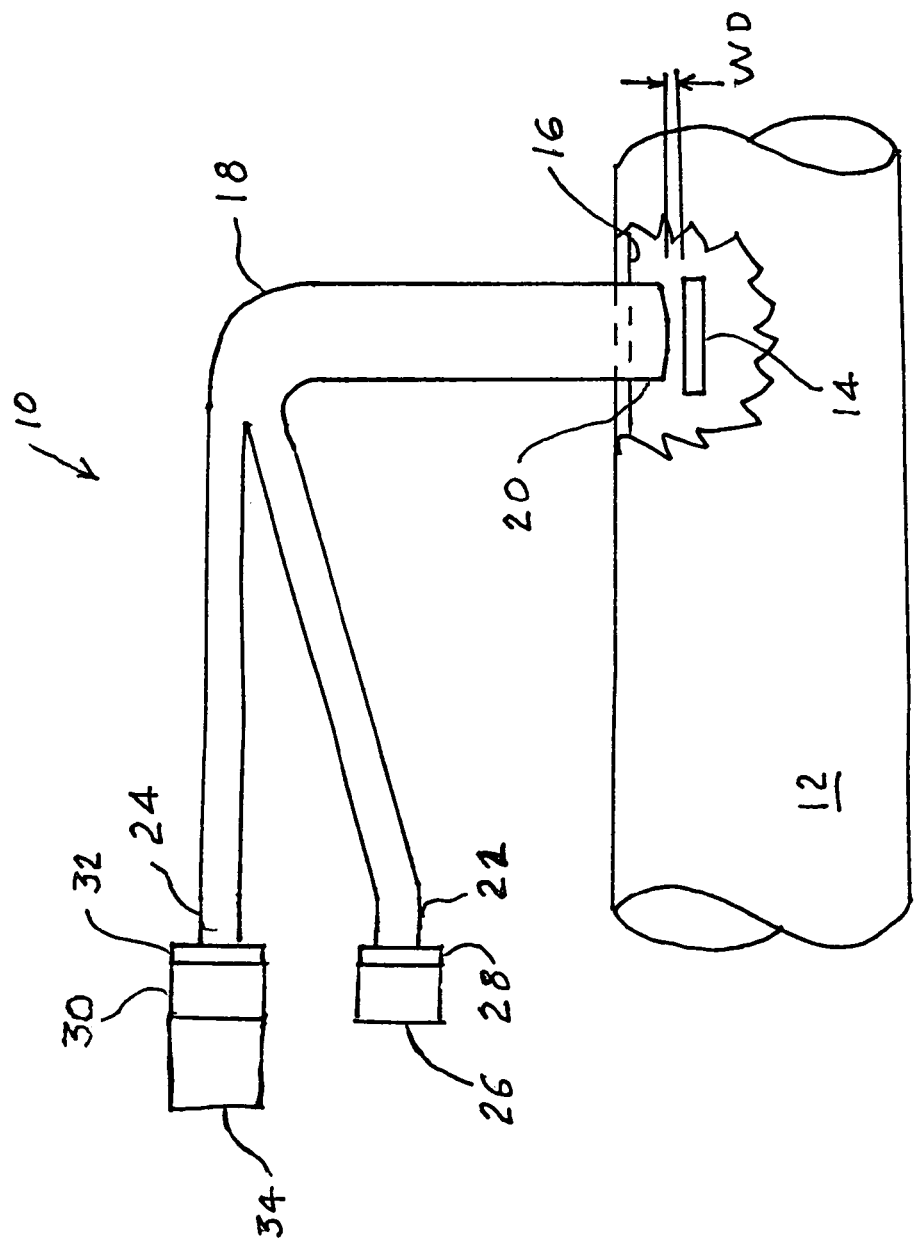
FIG. 1 is a schematic diagram of an optical fiber biofilm sensor system in accordance with the principles of this invention including a bacterial target substrate in relation with an interrogation fiber.

FIG. 1 shows an apparatus 10 having a fluid line 12 with a bacterial target substrate 14 located close to the interior surface wall 16 of the fluid line 12. A bifurcated optical fiber cable 18 carries at least one and preferable several optical fibers for transmitting the excitation signal (delivering optical fibers) and also at least one and preferable several optical fibers for carrying the emission signal (responding optical fibers). The distal end 20 of the bifurcated optical fiber cable 18 is located inside the fluid line 12 with the end 20 placed a working distance (WD) from the bacterial target substrate 12. The working distance is a distance sufficient to deliver the interrogating excitation light to bacteria on the bacterial target substrate 14 from the delivering optical fibers to cause autofluorescence and to effectively receive the autofluorescent emissions. In the case of the responding optical fibers. Of course in some configurations, the working distance for the delivering optical fibers and for the responding optical fibers may differ; but the term working distance is intended to mean a distance with respect to each that works.

The optical fiber cable 18 has first and second proximal ends 22 and 24. The proximal end 22 is connected to a light source 26 which may be an LED or a laser. A short pass filter 28 is interposed between the light source and the delivering optical fibers in order to filter out any light from the light source 26 that is in the range of the emission signal. The proximal end 24 is connected to a photodetector 30. A long pass filter 32 is interposed between the emission optical fiber proximal end 24 and the photodetector 30 in order to filter out any excitation light that may have entered the responding optical fibers. In operation, light from source 20 is directed at the bacterial target substrate 14 and autofluorescent emissions from bacteria on the bacterial target substrate 14 is detected by photodetector 30. The emission signal can be further measured and processed by the receiver/processor 34 that may include circuitry for additional processing and a specially programmed CPU for operating an algorithm to, for example, activate an alarm, an automatic diverter to substitute an alternative fluid line, to shut off the fluid process, etc.

The effectiveness of the system depends on the structure and location of the bacterial target substrate 14 to provide a preferred bacteria accumulation site and the structure and location of distal end 20 with respect to the substrate 14 to transmit light from the bacterial target substrate 14 at a frequency which is a function of the presence of bacteria there. It is considered preferable that the bacterial target substrate 14 be close to the wall 16 of the fluid line 12 in order to be exposed to slower moving fluid.

In one embodiment the bifurcated optical fiber 18 is an optical fiber cable having a number of optical fibers. One or more, preferably several, of the optical fibers are arranged to receive at their proximal end 22 the excitation signal; these are called excitation optical fibers. One or more, preferably several of the optical fibers are arranged to receive and deliver the autofluorescent signal, the emission signal to the proximal end 24; these are called emission optical fibers. At the distal end 20 the excitation fiber(s) and the emission fiber(s) are spaced an appropriate working distance from the bacterial target substrate 14 area to perform their respective functions.

Figure 2:
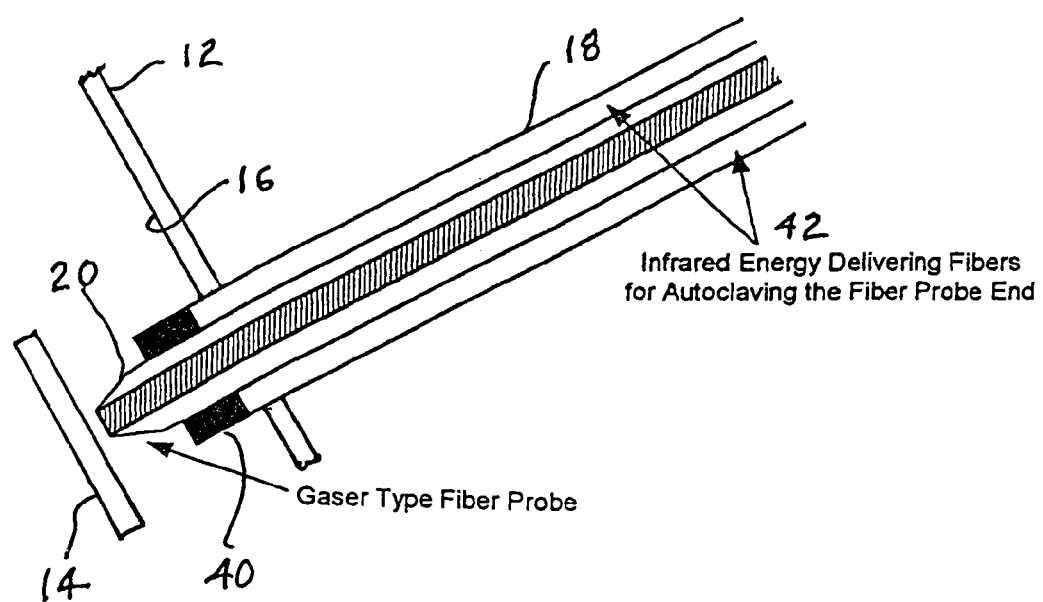
FIG. 2 is a schematic sectional side view of a portion of the system of FIG. 1 showing the detail of the interrogation fiber end.
Figure 3:
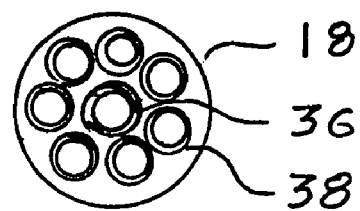
FIG. 3 is a schematic end view of a portion of one embodiment of an optical fiber cable used in the system.
Figure 4:
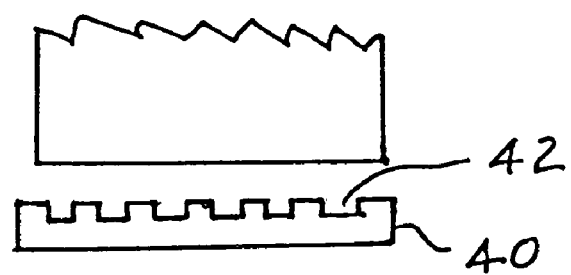
FIGS. 4, 5 and 6 are schematic side views of alternate configurations of the arrangement of the optical fiber cable and the bacterial target substrate in accordance with the principles of this invention.
Figure 5:
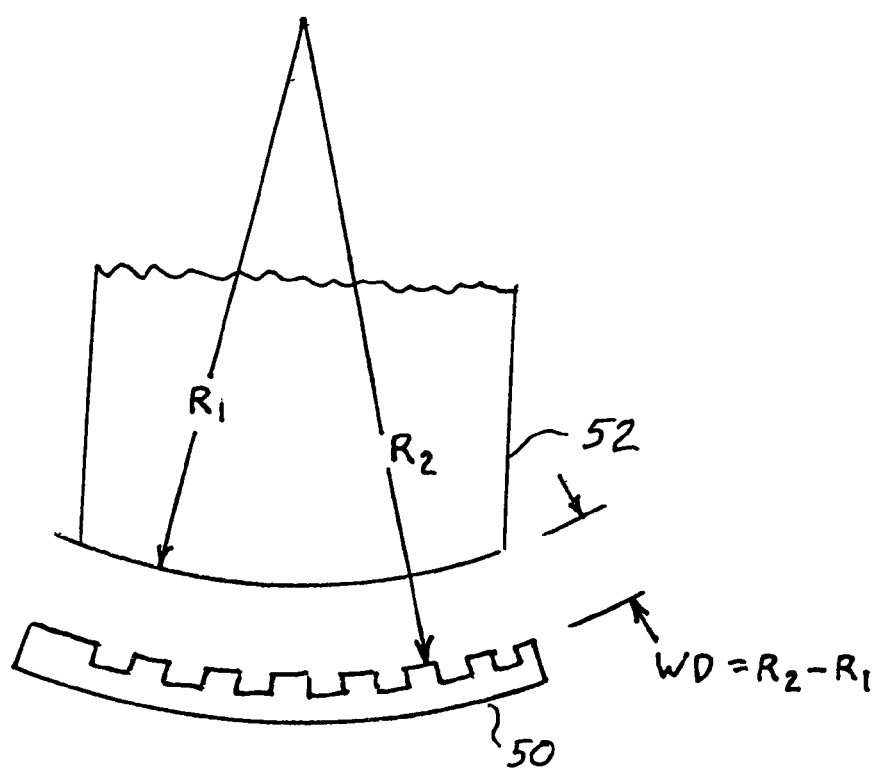
Figure 6:
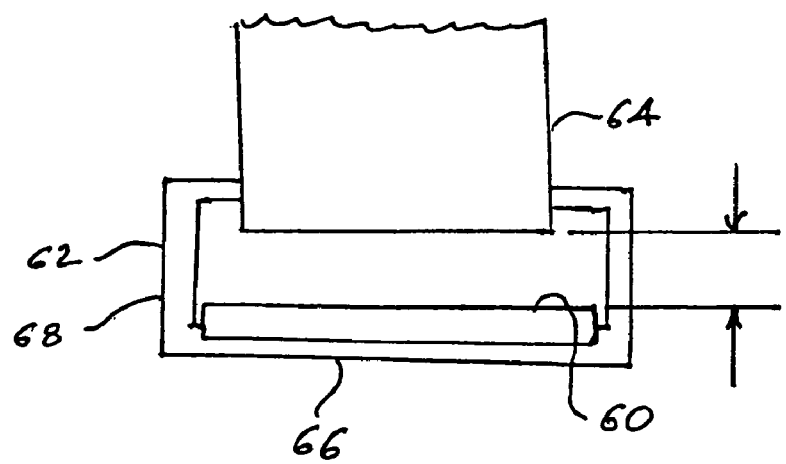

FIGS. 2 and 3 show views of the distal end 20 of the optical fiber cable 18 as well as the location of the distal end with respect to the bacterial target substrate 14. In FIG. 4 an exemplary configuration is a single excitation fiber 36 centrally located and a plurality of emission fibers 38 surrounding the excitation fiber 36. FIGS. 4 through 6 show alternative bacterial target structures.

FIG. 4 shows a schematic side view of a bacterial target substrate 40 in accordance with the principles of this invention. The bacterial target substrate 40 comprises a surface 42 of which is configured to include traps with feature size of from one to one hundred micrometers in a periodic or an a periodic arrangement to enhance the colonization rate of bacteria.

FIG. 2 shows a distal end 20 of an optical fiber cable 18 comprising a fiber bundle, the end view of which is shown in FIG. 3. The bundle includes a central excitation fiber 36 (although it is preferable to have a plurality of excitation fibers) through which the excitation signal is transmitted from source 28. The excitation signal from source 28 has a frequency in a range of from about 290 nm to about 420 nm, more preferably from about 340 nm to about 410 nm. In the signal path the short pass (excitation) filter 28 is between the excitation light source 26 and the bacterial target substrate 14 and is shown illustratively on the surface of the source (LED or laser).

Light from source 28 impinges substrate 14 which when bacteria is present responds by autofluorescence to emit light having an emission peak between 450 and 460 nanometers. Detector 30 of FIG. 1 measures the bacteria by autofluorescent emission from hydrogenated nicotinamide adenine dinucleotide (NADH) and/or from hydrogenated nicotinamide adenine dinucleotide phosphate (NADPH) emission by detecting the totality of the light intensity in the wavelength range of 420 to 550 nanometers; thereby defining an emission signal whose intensity has a relationship with the amount of bacteria on the substrate. To this end, detector 30 includes a long pass (emission) filter 32, shown in FIG. 1, with a cut off between 400 and 440 nanometers.

The light from substrate 14 is transmitted to detector 30 via emission optical fibers 38 shown in FIG. 3 and advantageously configured as a fiber bundle around the centrally located excitation optical fiber 36 as shown in FIG. 3.

Another preferred configuration of the optical fibers in the optical fiber cable is a pseudo-random configuration in which the excitation fibers and the emission fibers are intermixed either in a pattern such as concentric circles or more randomly. The arrangement of the fibers at the distal end is what is of concern; their arrangement path getting there is not important.

The working distance (WD) between distal end 20 of the fiber cable 18 and the substrate 14 is approximately 0.5 millimeters (mm) for an optical fiber distal end consisting of randomly arranged fibers of forty micrometers of NA=0.5 and a bundle diameter of 0.18 inch. For practical embodiments herein, a working distance typically lies between 0.1 mm and 10 mm.

Figure 7:
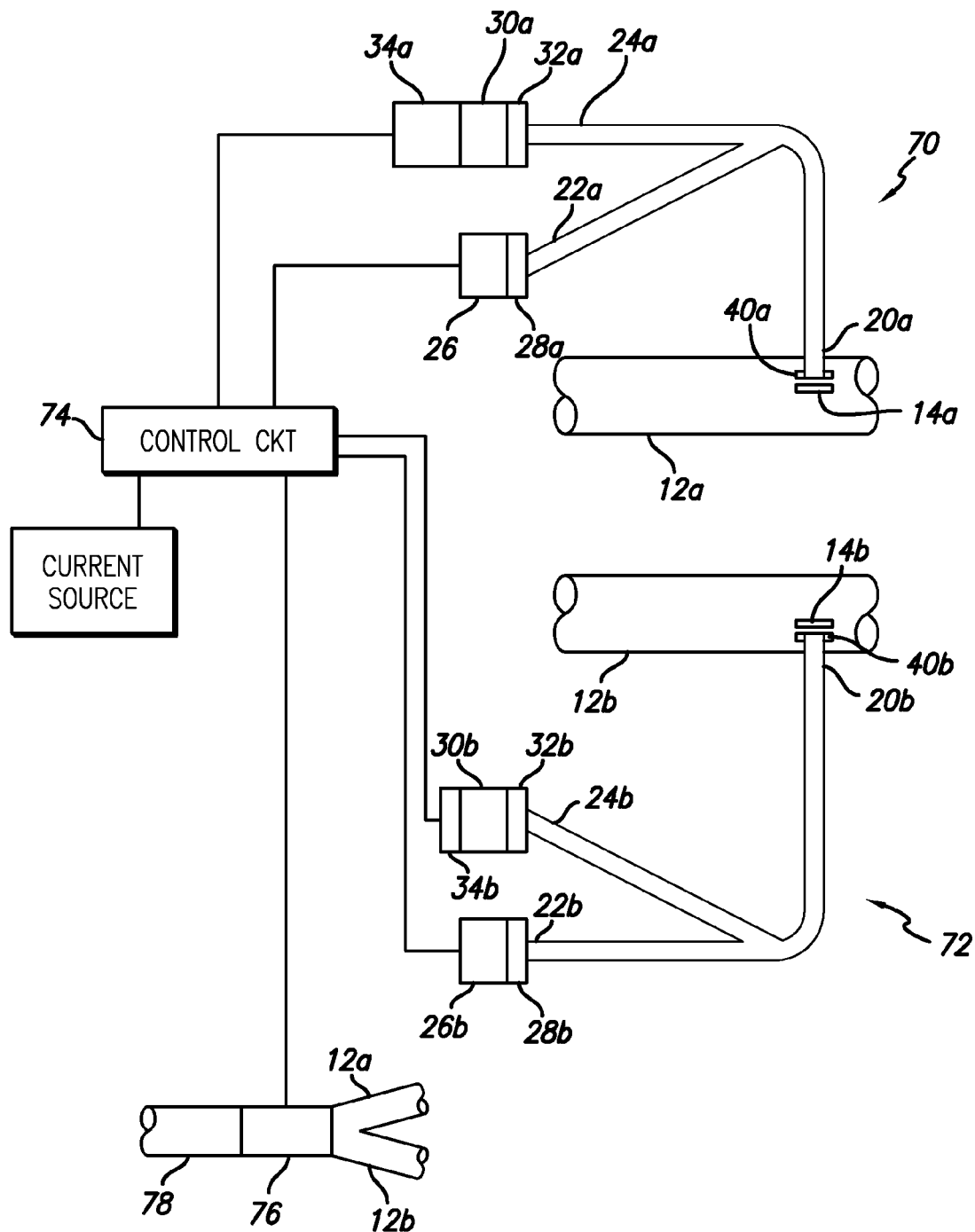
FIG. 7 is a schematic diagram of a diverter system for changing the fluid path from a contaminated to a non-contaminated path in order to remediate a system without loss of operation.

FIG. 7 is a schematic diagram of a system of the type shown in FIG. 1 further including an auxiliary fluid line, a diverter for redirecting fluid flow from one fluid line to another and a heating mechanism for eliminating bacteria from the on line path. For convenience, like reference numbers are used in FIG. 7 corresponding to designations of like elements in FIG. 1 with subscripts to differentiate primary (on-line) and alternative (off line) subsystems.

Specifically, FIG. 7 shows a bacteria sensing system including, illustratively, an on-line or primary subsystem 70 and an off line or alternative subsystem 72. Each subsystems, 70 and 72 of the system is associated with a water line 12a and 12b respectively. Each subsystem also includes a bacterial target substrate 14a and 14b respectively. Excitation light from source 26a or 26b is directed at the respective substrate 14a and 14b depending on which subsystem is in operation (hereinafter assumed to be subsystem 70). Signal response from substrate 14a is directed at photodetector 30a through a long pass filter 32a (32b for subsystem 72) and is processed by processor 34a (34b for subsystem 72). The presence of a signal at a frequency representative of the presence of bacteria at substrate 14a, results in photodetector 30a and processor 34a signaling control circuit 74 to activate diverter 76 to divert the fluid flow from fluid source 78 to from fluid line 12a to fluid line 12b thus taking subsystem 70 off-line. Of course, the reverse process switches from subsystem 72 to subsystem 70. But in some cases subsystem 72 may be configured as a temporary subsystem until the primary subsystem 70 has been remediated and can be put back on line.

Each of the fluid lines 12a and 12b is associated with a sensing system operating as described hereinbefore in connection with FIG. 1. As shown in FIG. 2, each sensing system includes an optical fiber, illustratively, with a metallic collar 40 at distal end 20 as shown in FIG. 2. Infrared delivery fibers 42 are coupled to collar 40. Control circuit 74 responds to a signal from the processor 34a to activate a source of infrared energy to heat collar 40 to a temperature and for a time to eliminate bacteria on the associated bacterial target substrate 14a (or 14b for subsystem 72).

The off-line subsystem 72 of FIG. 7 is thus readied for on-line operation if and when photodetector 30a receives a signal indicating the presence of bacteria on the substrate 14a and the processor 34a recognizes a sufficient level of bacterial presence as indicated by the intensity of the emission signal to trigger the procedure of taking the primary subsystem 70 offline and substituting the alternative subsystem 72. At the same time, the remediation process is also triggered. When remediation is triggered near infrared light (NIR), at wavelength 980 nm or 1.06 um, is send down the optical fibers 42 (FIG. 2). As this is a water absorption line, the biofilm on the substrate 14a which is mainly water will heat up. The temperature is measured by and with a thermocouple controlled to hold temperature at 125 degrees C. and to stop heating. This can be accomplished by measuring temperature with a thermocouple or with fluorescence emitted by a phosphor located at the distal end 20a where fluorescence intensity is calibrated against temperature.

Figure 8:
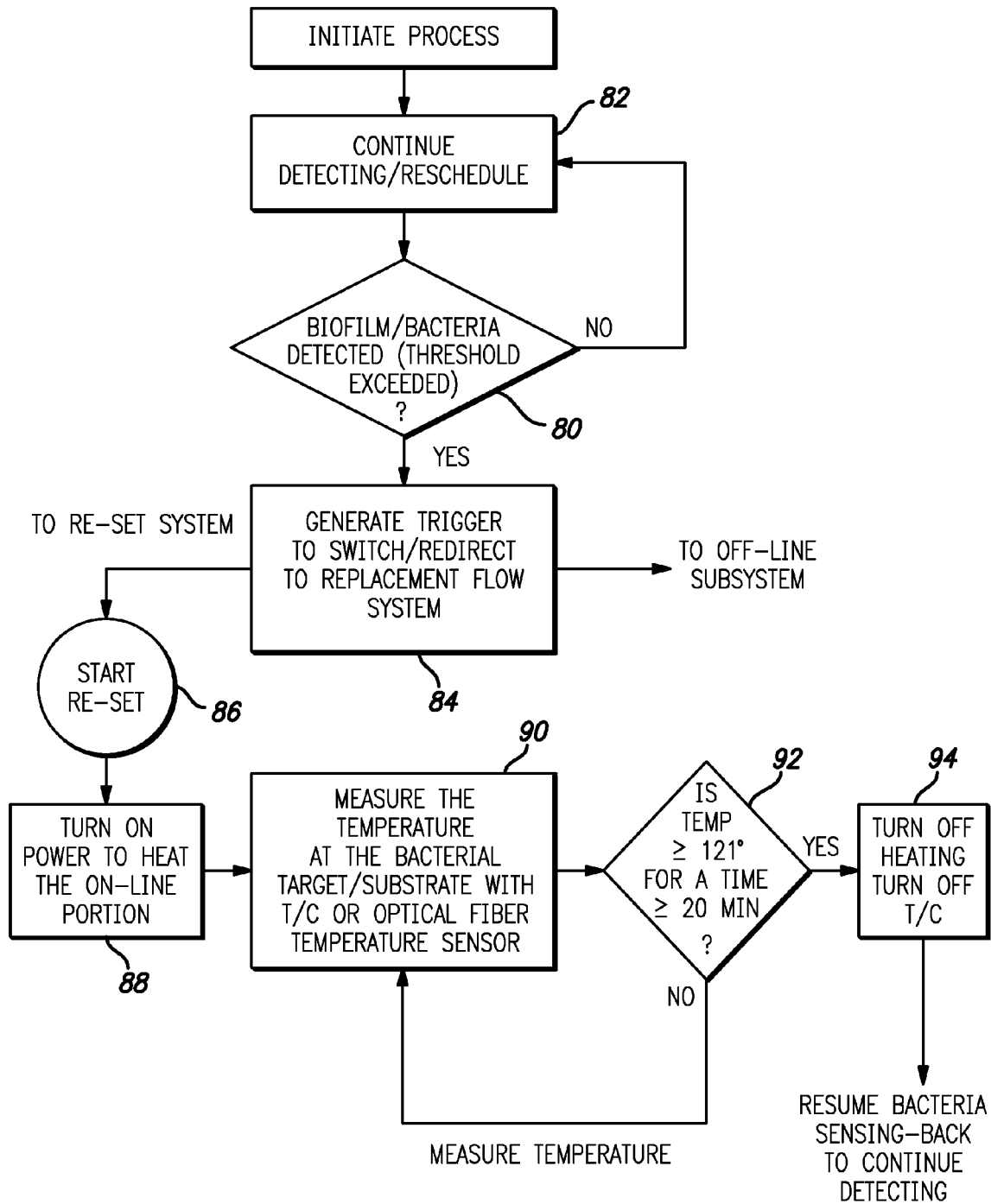
FIG. 8 is a flow diagram for the operation of the system FIG. 7.

FIG. 8 is a flow diagram of the operation of the system of FIG. 7. Excitation light from source 26a, (in the assumed on-line subsystem 70) is generated in accordance with a user-selected schedule to test for the presence of bacteria as indicated in block 80 of FIG. 8. If no response is detected, the detection operation continues or is rescheduled as indicated by block 82.

If bacteria is detected, a signal is generated to divert fluid flow to the sterile off-line subsystem as indicated in block 84.

The signal also initiates the sterilization of the previously on-line subsystem substrate as indicated in block 86 resulting in the activation of an illustrative infrared (laser, LED—) source to heat the contaminated substrate as indicated in block 88.

The temperature at the distal end of the optical fiber may be measured, with a T/C or other sensor, as indicated in block 90 to ensure that a temperature of at least 125 degree Celsius has been reached for at least 20 minutes as indicated in (decision) block 92.

If the minimum temperature and time has been reached, the infrared source is turned off as indicated by block 94 and the bacteria detection operation is resumed for the (now) on-line subsystem. If not, the temperature sensing operation continues.

FIGS. 4 and 5 show illustrative configurations for a bacterial target substrate for the system of FIG. 1 or FIG. 7. FIG. 4 shows a substrate 40 with a periodic or random microstructure as discussed hereinbefore. FIG. 5 shows a substrate 50 with a curved surface of radius R2 and the distal end 52 of the optical fiber cable having a radius R1; with a working distance, WD, being R2-R1. FIG. 6 shows a substrate 60 with a flat surface of dark (no shine) material such as polycarbonate, black silicone or anodized aluminum. A fiber associated with such a substrate conveniently has a support and distance structure 62 attached to the distal end 64 of the fiber cable and having a table 66 on which is mounted the substrate 60 and locating arms 68 to establish the working distance.

Regardless of the probe configuration, it is preferable to mount it near the interior surface of the fluid line. If the fluid line is transparent to the frequency used for detection, placement of the probe is straightforward. On the other hand, if the fluid line is not transparent, the probe has to be mounted on a transparent patch and secured about an aperture in the line wall.

The detection of a signal representative if the presence of bacteria has been described in terms of a photodetector. Alternative detection techniques also are useful such as a spectrometer comprising one or more grating monochromaters and one or more photodetectors.

Alternative techniques for measuring the temperature of the probe during sterilization are available. One illustrative technique utilizes a phosphor coated on the probe substrate. The phosphor emits a fluorescence of an intensity which is a function of its temperature and which can be calibrated for the system.

The various components of FIG. 1 or FIG. 7 may be any such components capable of operation as described and the components described herein are only illustrative.

Another aspect of the invention recognizes that the sensor element of the system is subject to contamination in the above described configurations and that if the distance between the sensor and the biofilm is in the fluid path, scattering of the emission signal can occur. Therefore a further embodiment of the invention places the sensor outside the fluid path with the substrate for the biofilm inside the fluid path. In more particular form, the sensor is placed at adjacent to the outer surface of a transparent (that is, transparent to the excitation and the emitted light) wall portion. The substrate is integral with an inner surface of the transparent wall portion so as to provide a direct light path through the transparent wall portion with no fluid flowing between the substrate and the transparent wall portion. The distance from the sensor to the substrate is designed for the correct working distance (WD). It is desirable that the sensor be in good optical contact with the transparent wall portion, preferably that the sensor end is in physical abutment with the transparent wall portion.

The biofilm target substrate in one embodiment is formed as part of the transparent wall portion. In other embodiments it may be a separate piece placed in good optical contact with the transparent wall portion.

Figure 9:
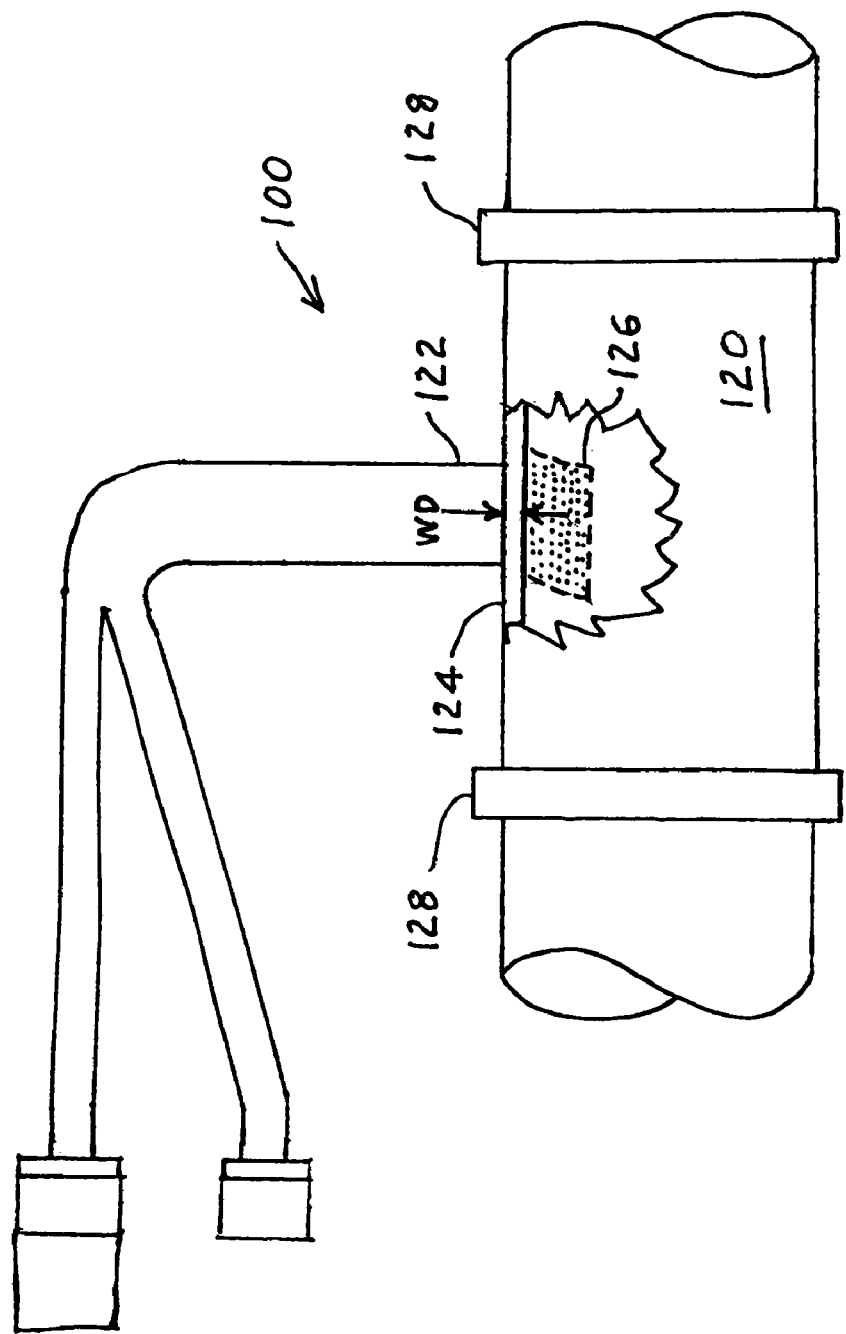
FIG. 9 is a schematic representation of a biofilm detection and remediation system in accordance with the principles of the invention.

FIG. 9 is a schematic representation of a biofilm detection and remediation system 100 in accordance with the principles of the invention. The system is designed to detect the accumulation of biofilm in a fluid conduit 120. In the illustrated embodiment the fluid conduit is transparent. The sensor 122 is in intimate contact with the outer surface 124 of the transparent conduit 120. A portion of the inner surface of the fluid conduit 120 is configured as a biofilm target substrate 126. In the preferred embodiment the biofilm target substrate 126 is a getter affinity surface for bacteria. The term getter and the term affinity surface are used interchangeably to indicate that the biofilm target substrate has been made to cause the colonization of bacteria at an accelerated rate, the term getter affinity surface will also be used to define the biofilm target substrate when it is specially configured or prepared to attract bacteria colonization at an accelerated rate. As such it encompasses any instrumentality that will have an affinity for bacteria. The preferred material for the transparent wall portion is a glass.

The wall thickness of the fluid conduit 120 at least in the area of the biofilm target substrate 126 is such as to provide a correct working distance between the end of the sensor and the substrate 126 operative for the excitation signal from the sensor 122. The sensor system 100 otherwise is as described above.

A number of configurations are possible with the invention as broadly described above. In the configuration of FIG. 9, an entire conduit portion is transparent. It is made so as to be inserted in a fluid system with connectors or joints of any convenient type, shown schematically at 128.

Figure 10:
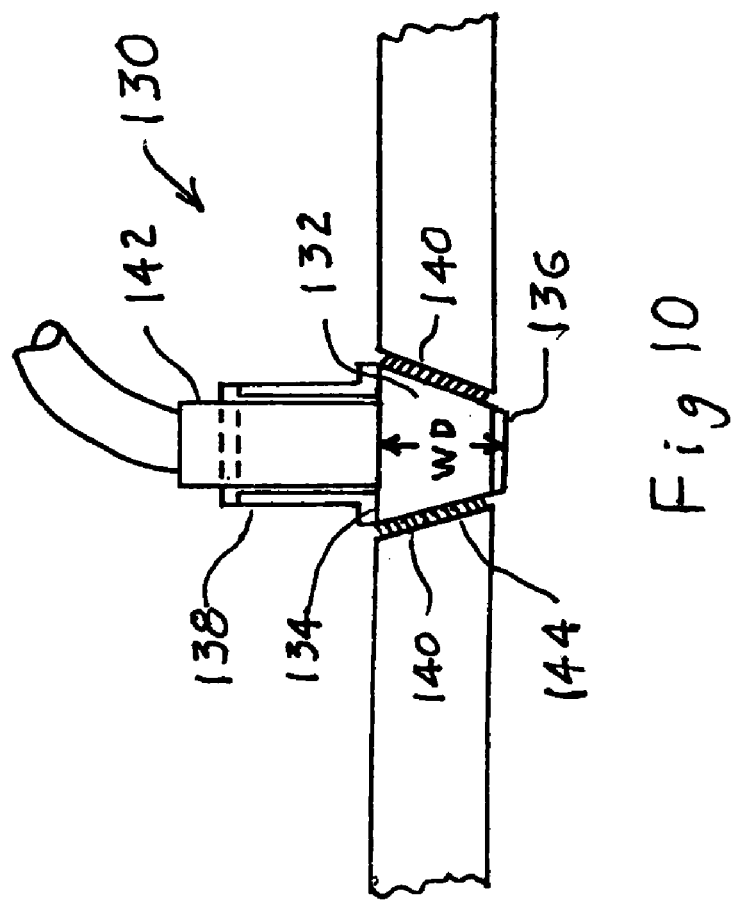
FIG. 10 is a schematic representation of a transparent wall feature in accordance with the principles of the invention.

Another configuration using the transparent wall feature of the invention is shown in FIG. 10. In that configuration, a disposable or reusable cell 130 is defined. The cell 130 has a transparent wall element 132 having an outer surface 134 and an inner surface 136. Attached to the outer surface 134 is a sensor receptacle 138. The inner surface 136 in the shown embodiment is made as the biofilm target substrate preferable as a bacteria getter affinity surface, as an integral part of the transparent wall element 132. The term "integral part" includes both a substrate that is formed in the transparent wall element itself, and one that is a separate piece and is attached. In the shown embodiment, the transparent wall element 132 is circular and tapered. It fits into a mating aperture 144 in a conduit that could be part of the fluid system or could be added to the fluid system. Fitting and sealing elements are also needed, but these may be designed in conventional forms and are indicated at 140 around the periphery of the transparent wall element 132. A mechanical hold-down device (not shown) may be used.

In use the optical fiber sensor head 142 is inserted into the receptacle 138, and held in place by a retaining structure (not shown) in or as part of the receptacle that will press the fiber ends against the outer wall surface 134 sufficiently to allow good signal transmission. The cell 130 is then (or prior to insertion of the sensor head) placed in the aperture 144. The system as above described (see FIGS. 7 and 8 and description) is implemented to provide excitation light and the emission from the biofilm is returned. A greater density or thickness of biofilm will return a higher intensity signal that can be measured against preset limits to provide an alarm that will cause the system operator to commence a remediation procedure, or the alarm can be integrated to automatically commence a remediation procedure.

Figure 11:
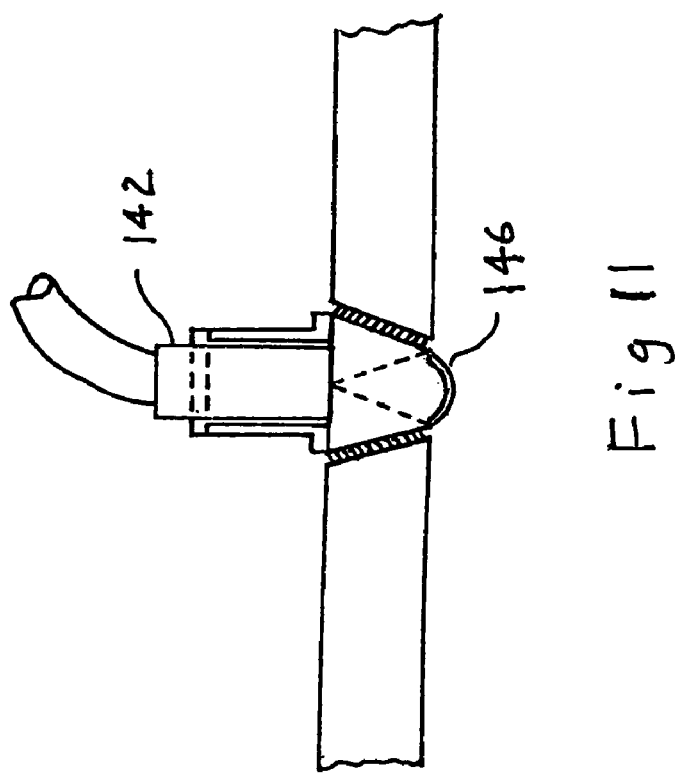
FIG. 11 is a schematic representation of a transparent wall feature in accordance with the principles of the invention.

As noted above, scattering can be a problem in obtaining the emitted signal. A means for avoiding or at least diminishing scattering is shown in FIG. 11. In this embodiment, the substrate 146 is curved so as to focus the emitted signal at the sensing end of the sensor head.

As noted above a goal of the present invention is to grow bacteria faster at the sensor than elsewhere in the fluid system. With greater bacteria presence, more of the autofluorescent biomarker material NADH and NADPH will be present. The intensity of the returning emitted signal will increase with greater amount of autofluorescence, that is, with greater density or thickness layer of NADH and NADPH.

There are two general approaches to raise bacterial affinity to the biofilm target substrate: physical and chemical. These can be used individually or in combinations. The physical approach essentially increases the surface area of the region of interest and provides favorable environment for accelerated bacterial growth. This can be achieved by:

A pattern of cavities in the surface of the substrate. The cavities can be made as a repeating pattern or several different patterns, or grooves, channels or ridges in the surface; and adding an additional, cell growth-promoting layer onto the surface.

As described above the substrate is created as a getter affinity substrate using physical configuration by creating cavities in a predetermined configuration, such as a regular pattern. The cavities can be discrete in, for example circular or rectilinear form. The cavities can be linear as grooves. The cavity lateral dimensions in the plane of the substrate should be in the range of about 5-10 microns in the case of discrete cavities, and about 5-10 microns wide in the case of groove cavities. The cavities (and grooves) should have a depth of up to about 10 microns. Surface area can also be increased by adding a porous membrane to the surface of the glass that is optically transparent, regardless of whether liquid flows through or past it. One example of an optically transparent membrane is Whatman's Anopore inorganic aluminum oxide membranes.

Chemical approaches to increasing bacterial affinity provide favorable surfaces to which the nascent biofilm can attach. Since biofilms excrete polysaccharides to form their anchoring exosaccharides, thin-layers of glycophilic substances stuck to the glass surface can encourage growth. The basic methods of applying bio-adhesives can use a biochemical or a chemical approach:

biochemical: killed, already attached biofilm; and chemical: covalently bonded glycopolymers or essential amino acids.

Biofilm previously grown onto a surface has the advantage of having the best chemical match for bacterial exosaccharides. Care, however, must be taken to kill this biofilm without weakening the exosaccharide anchor (i.e. brief UV irradiation) The major disadvantage of killed biofilm is that most killing techniques also weaken the structural integrity of polysaccharides.

Chemical modification of the surface is possible by silanization, in which covalent bonds are made to the glass surface. Silanes are commercially available in staggering variety and can be synthesized readily and cheaply in any laboratory. Functionalizing these silanes with bacteria-friendly groups would satisfy the goal. At least two classes of compounds would attract bacteria: "sticky" end glycosides and growth-stimulating peptides, both of which can be bonded to appropriately silanized surfaces. "Sticky" glycosides have available functionalizable groups on the saccharide molecule to which bacteria can then glycosidically add its own polysaccharides. "sticky" glycosides can include glucose, galatose, xylose, cellubiose, and maltose. Growth-stimulating amino acids and peptides essential to bacterial growth are also easily anchored to glass via silane adhesives. Polysaccharide adhesion is another coating material that causes bacteria to adhere to the getter affinity surface.

As will be apparent, the signal processing described above is applicable to all the embodiments of the sensing configurations.

The foregoing Detailed Description of exemplary and preferred embodiments is presented for purposes of illustration and disclosure in accordance with the requirements of the law. It is not intended to be exhaustive nor to limit the invention to the precise form(s) described, but only to enable others skilled in the art to understand how the invention may be suited for a particular use or implementation. The possibility of modifications and variations will be apparent to practitioners skilled in the art. No limitation is intended by the description of exemplary embodiments which may have included tolerances, feature dimensions, specific operating conditions, engineering specifications, or the like, and which may vary between implementations or with changes to the state of the art, and no limitation should be implied therefrom. This disclosure has been made with respect to the current state of the art, but also contemplates advancements and that adaptations in the future may take into consideration of those advancements, namely in accordance with the then current state of the art. It is intended that the scope of the invention be defined by the Claims as written and equivalents as applicable. Reference to a claim element in the singular is not intended to mean "one and only one" unless explicitly so stated. Moreover, no element, component, nor method or process step in this disclosure is intended to be dedicated to the public regardless of whether the element, component, or step is explicitly recited in the Claims. No claim element herein is to be construed under the provisions of 35 U.S.C. Sec. 112, sixth paragraph, unless the element is expressly recited using the phrase "means for . . . " and no method or process step herein is to be construed under those provisions unless the step, or steps, are expressly recited using the phrase "step(s) for . . . "

What is claimed is:

1. Apparatus for detecting biofilm in a fluid system comprising;

a wall portion having an outside surface outside the fluid flow and an inside surface in contact with the fluid flow and being transparent to excitation and emitted light;

a biofilm target substrate integral with the inside surface in contact with fluid in the fluid system;

an optical fiber sensor in optical contact with the outside surface and having at least one fiber (excitation fiber) for sending excitation light through the wall portion to the biofilm substrate and at least one fiber for receiving emitted autofluorescence from the biofilm caused by the excitation light (emission fiber).

2. The apparatus of claim 1 wherein the biofilm target substrate is a getter affinity substrate.

3. The apparatus of claim 2 wherein the getter affinity substrate has cavities for promoting the growth of bacteria in the cavities.

4. The apparatus of claim 2 wherein the getter affinity substrate has sticky glycosides for promoting the growth of bacteria.

5. Apparatus for detecting biofilm in fluid systems comprising;
- a detection cell having a transparent wall portion and being configured to fit in an aperture in a fluid carrying conduit the transparent wall portion having an outside surface and an inside surface;
- a biofilm target substrate on the inside surface enabled to allow the growth of biofilm;
- a receptacle for attaching a fiber optic sensor head in optical communication through the wall portion to the surface portion on the inside surface.

6. The detection cell of claim 5 further wherein the biofilm target substrate on the inside surface is a getter affinity substrate.

7. The apparatus of claim 6 wherein the getter affinity substrate has cavities for promoting the growth of bacteria in the cavities.

8. The apparatus of claim 6 wherein the getter affinity substrate has sticky glycosides for promoting the growth of bacteria.

* * * * *